US010010650B2

United States Patent
Capel et al.

(10) Patent No.: US 10,010,650 B2
(45) Date of Patent: Jul. 3, 2018

(54) COMPOSITE HEMOCOMPATIBLE MATERIAL AND METHOD FOR ITS PRODUCTION

(75) Inventors: Antoine Capel, Clamart (FR); Alain Carpentier, Paris (FR); Marion Melot, Paris (FR)

(73) Assignee: Carmat, Velizy Villacoublay (FR)

( * ) Notice: Subject to any disclaimer, the term of this patent is extended or adjusted under 35 U.S.C. 154(b) by 2393 days.

(21) Appl. No.: 12/093,306

(22) PCT Filed: Nov. 7, 2006

(86) PCT No.: PCT/FR2006/002471
§ 371 (c)(1),
(2), (4) Date: May 9, 2008

(87) PCT Pub. No.: WO2007/054637
PCT Pub. Date: May 18, 2007

(65) Prior Publication Data
US 2008/0279910 A1    Nov. 13, 2008

(30) Foreign Application Priority Data

Nov. 10, 2005 (FR) ...................................... 05 11430

(51) Int. Cl.
*A61L 31/16* (2006.01)
*A61L 27/36* (2006.01)
*A61F 2/24* (2006.01)
*A61L 33/18* (2006.01)

(52) U.S. Cl.
CPC ........ *A61L 27/3604* (2013.01); *A61F 2/2415* (2013.01); *A61L 27/3683* (2013.01); *A61L 33/18* (2013.01); *A61L 2430/40* (2013.01)

(58) Field of Classification Search
None
See application file for complete search history.

(56) References Cited

U.S. PATENT DOCUMENTS

| 4,059,457 | A | * | 11/1977 | Austin ....................... 106/162.2 |
| 4,197,658 | A | * | 4/1980 | Fraser ............................... 34/92 |
| 4,588,404 | A | * | 5/1986 | Lapeyre ....................... 623/3.21 |
| 5,135,539 | A | | 8/1992 | Carpentier |
| 5,256,418 | A | | 10/1993 | Kemp |
| 5,851,230 | A | | 12/1998 | Weadock |
| 6,699,276 | B2 | * | 3/2004 | Sogard et al. ............... 623/1.13 |
| 8,007,992 | B2 | * | 8/2011 | Tian et al. ..................... 435/1.1 |
| 8,153,591 | B2 | * | 4/2012 | Masters et al. .............. 514/17.2 |
| 8,597,720 | B2 | * | 12/2013 | Hoffmann et al. ............ 427/2.3 |
| 2013/0042957 | A1 | * | 2/2013 | Melot et al. ..................... 156/60 |

FOREIGN PATENT DOCUMENTS

| DE | 39 07 718 | 9/1989 |
| EP | 0 282 091 | 9/1988 |
| EP | 0 457 430 | 11/1991 |

OTHER PUBLICATIONS

Motlagh et al. (J. Biomed Mater Res., 82A:907-916, 2007.*
Motlagh et al. (Biomaterials, vol. 27, iss. 24, Aug. 2006, pp. 4315-4324).*
Ratcliffe et al. (Matrix Biology, vol. 19, 2000, pp. 353-357) Yin et al. (J. Biomed. Material Res. Part B:Appl Biomater, vol. 00B, iss. 00, 2014, pp. 1-9).*
Lin et al. (Artificial Organs, vol. 25, No. 8, pp. 617-621).*
Reece et al. (The Am. J. of Surgery, vol. 182, 2001, 40S-44S).*
Shin et al. (Biomaterials, vol. 24, 2003, pp. 4353-4364).*
International Search Report dated Feb. 28, 2007 w/ English translation.

\* cited by examiner

*Primary Examiner* — Hope Robinson
(74) *Attorney, Agent, or Firm* — Dickinson Wright, PLLC

(57) ABSTRACT

Disclosed is a composite hemocompatible material and a method for producing a composite hemocompatible material. The composite material includes a synthetic substrate and an animal biological tissue. The animal biological tissue is interlinked the synthetic substrate so as to bond the animal biological tissue to the synthetic substrate and form the composite hemocompatible material.

12 Claims, No Drawings

COMPOSITE HEMOCOMPATIBLE MATERIAL AND METHOD FOR ITS PRODUCTION

CROSS-REFERENCES TO RELATED APPLICATIONS

This application is a national stage filing under 35 USC 371 of International Application No. PCT/FR2006/002471, filed Nov. 7, 2006, which claims the benefit, under 35 USC 119, of the filing date of French Application No. 05 11430, filed Nov. 10, 2005, the contents of which are fully incorporated herein by reference.

FIELD OF THE INVENTION

The present invention relates to a hemocompatible material and to a method for producing a hemocompatible material. In particular, the invention relates to a composite hemocompatible material and a method for producing a composite hemocompatible material.

BACKGROUND OF THE INVENTION

It is known that blood is a very sensitive living liquid tissue and that it is readily altered when coming into contact with chemical substances or when exposed to mechanical stresses, for example shear stresses; it coagulates upon contact with most inert materials or during stases. In reality, very few hemocompatible materials exist and most of them require a patient carrying such hemocompatible material to take anticoagulants.

It is also known (see, for example, document U.S. Pat. No. 5,135,539) that cardiac prostheses exist in which the artificial ventricles comprise flexible membranes actuated by pulses of a fluid so as to cause movement of the blood. In this case, the hemocompatibility of said membranes is particularly essential, due to the fact that the membranes are mobile and in contact with a complex and often turbulent blood flow.

In the art, substantially hemocompatible materials which are either synthetic or of biological origin are known.

The synthetic materials are generally polyurethane elastomers or silicone elastomers; they are used either with a smooth surface, in order to reduce platelet or blood adhesions, or with a porous surface, in order to allow the adhesion of a biological layer capable of serving as an interface with the blood. Such synthetic materials have good qualities of flexibility, impermeability and deformability, but require the use of anticoagulants.

Material of biological origin includes, but is not limited to, animal tissue and biological material derived from animal tissue, for example collagen.

Tissues of animal nature have to be chemically fixed (most commonly with glutaraldehyde) when they are intended to be implanted into the human body, in order to prevent immunological reactions. Such biological materials thus treated generally have excellent hemocompatible properties and do not require, moreover, the use of anticoagulants, but they are absolutely not impermeable.

Conversely, "hemocompatible and implantable" synthetic materials generally have advantageous mechanical and leaktightness characteristics, but are tolerated in the blood stream only by means of a strict anticoagulation.

In order to be able to benefit from the good mechanical and leaktightness properties of synthetic materials and from the good hemocompatibility characteristics of materials of biological origin, document U.S. Pat. No. 5,135,539 envisions superimposing a membrane of synthetic material and a membrane of biological origin. However, such an arrangement leads to the formation of an intermediate chamber between said membranes, which can be the site of infections or of undesirable liquid collections.

SUMMARY OF THE INVENTION

The object of the present invention is to remedy the abovementioned drawbacks and relates to a flexible hemocompatible material that can be readily deformed and is completely impermeable.

In one embodiment, according to the invention, the hemocompatible material comprising a strong and leaktight synthetic substrate is notable in that it comprises a treated animal biological tissue chemically interlinked with said substrate, wherein a solvent is dispersed in the substance.

DETAILED DESCRIPTION OF THE INVENTION

Thus, by virtue of the present invention, a composite material is obtained, the hemocompatibility of which is provided by the biological tissue, while the mechanical strength and the leaktightness are provided by the synthetic substrate.

Although said synthetic substrate provides the mechanical strength of the composite material in accordance with the present invention, it is advantageous for the biological tissue to itself be strong. To this effect, this biological tissue can consist of animal pericardium, for example of bovine pericardium or of any other biological tissue.

Moreover, it is advantageous for the flexible synthetic substrate to be an elastomer. This elastomer can be a silicone elastomer or a polyurethane elastomer. However, for reasons of leaktightness, it is preferable to use the latter elastomer for producing said flexible synthetic substrate.

The manufacture of a composite hemocompatible material in accordance with the present invention comprises several steps:

1. The process is begun by chemically fixing, in a known manner, the biological tissue, preferably consisting of animal pericardium, with any suitable product, such as an aldehyde. In the latter case, glutaraldehyde is preferably used, for example at the concentration of 0.625%. Such chemical fixing provides the biological tissue with nonantigenicity, chemical, biological and physical stability and in particular resistance to variations in temperature and in mechanical stresses;

2. Next, the biological tissue is freeze-dried. The aim of this treatment is, firstly, to dehydrate it, which is essential for being able to cause it to adhere, but also to conserve the three-dimensional structure of said biological tissue after dehydration. In fact, when a biological tissue dehydrates under normal conditions, the collagen fibers that constitute it come into contact with one another and irreversible chemical bonds are created, making the subsequent rehydration of the biological tissue impossible. In order to avoid this drawback, the freeze-drying makes it possible to immobilize the structure of the pericardium by freezing, and then to remove the water at very low pressure by sublimation, therefore without allowing any mobility and therefore any rearrangement of the fibers. The two parameters which are essential to the control of the freeze-drying are the kinetics and dehydration:

the kinetics should be very slow—for example between 2° C./hour and 8° C./hour—in order to avoid any risk of superfusion (fusion of the water, leading to local rehydration);

the degree of dehydration should be at least equal to 75%, preferably of the order of 78% to 80%. Too low a degree of dehydration would allow a certain rehydration of the tissues and therefore a certain mobility of the fibers, which would be reflected in a loss of flexibility and poor rehydration after a storage phase (even short). Too great a dehydration would, for its part, denature the biological material and would lead to considerable shrinkage. The biological materials in fact consist of bound water (10% of solids and 10% of bound water for the pericardium) which is part of the actual constitution of the material and which it is not therefore necessary to remove.

In one embodiment, the biological tissue is first treated for several days with a glycol, advantageously polyethylene glycol, before being freeze-dried. The polyethylene glycol in fact creates low-energy bonds with the various collagen fibers and therefore interposes between these fibers like the bars of a ladder. During the freeze-drying, the various fibers cannot therefore interact with one another. Since these bonds are, however, low energy, the polyethylene glycol, although it is completely biocompatible (for certain molecular masses, according to the European Pharmacopeia), is readily rinsed out during rehydration;

3. Moreover, a layer of a dispersion of the constituent substance of said substrate in a solvent is deposited on said flexible synthetic substrate. If, as mentioned above, said substrate is a polyurethane elastomer, said dispersion contains implantable biocompatible polyurethane in a polyurethane-dependent solvent, which may be dimethylacetamide. This dispersion, which can be deposited on said substrate in any known manner (coating, spraying, etc.) has the aim of serving as a hemocompatible agent for adhesion with the biological tissue. Then, said freeze-dried biological tissue—which is impregnated with said dispersion—is applied to said layer of hemocompatible adhesion agent in order to ensure mechanical adhesion of said membrane on said substrate and to obtain said composite material;

4. After which, the solvent is removed from said hemocompatible adhesion agent, for example by hot drying, hot drying under vacuum and/or by hot extraction in physiological saline. Preferably, the removal of the solvent is obtained by slow hot extraction (for example of the order of 40° C.), followed by extraction under vacuum and completed by extraction in physiological saline;

5. Finally, the composite material is rehydrated with physiological saline, if this was not done during the solvent extraction phase.

In the method in accordance with the invention, described above, the treatment with polyethylene glycol and the freeze-drying make it possible to obtain a dry biological tissue which is completely rehydratable without impairment of said tissue and virtually without surface shrinkage. The bonding, by a mechanical anchoring, of said biological tissue by means of said dispersion, and not by means of an adhesive (purely chemical adhesion), makes it possible to obtain very good mechanical adhesion of the tissue without denaturation of the latter and without the addition of a supplementary product (adhesive). The combination of the various extraction techniques used allows optimal extraction of the solvents, even heavy solvents, without denaturing the tissue, either by overheating, or by water uptake.

The composite material thus obtained allies the excellent hemocompatible properties of the biological tissue with the mechanical and leaktightness properties of the synthetic substrate. The whole is, moreover, completely flexible and deformable.

What is claimed is:

1. A composite hemocompatible material comprising:
   a strong and leaktight synthetic substrate comprised of an elastomer substance selected from the group consisting of silicone and polyurethane, and
   a membrane animal biological tissue, wherein the membrane of animal biological tissue is adhered to said strong and leaktight synthetic substrate by a hemocompatible adhesion agent comprised of a dispersion of the elastomer substance in a solvent, said dispersion impregnating said membrane of animal biological tissue adhered to the strong and leaktight synthetic substrate.

2. A method for producing a composite hemocompatible material, the method comprising the steps of:
   treating a membrane of animal biological tissue with a glycol to introduce the glycol between fibers of said biological tissue;
   freeze-drying said glycol-treated membrane of animal biological tissue until a degree of dehydration of at least 75% is reached;
   providing a strong and leaktight synthetic substrate comprised of an elastomer substance selected from the group consisting of silicone and polyurethane;
   providing a hemocompatible adhesion agent comprised of a dispersion of the elastomer substance in a solvent; and
   applying said freeze-dried membrane of animal biological tissue on the strong and leaktight synthetic substrate with interposition of a layer of said adhesion agent, wherein the freeze-dried membrane of animal biological tissue is adhered to the strong and leaktight synthetic substrate, and the adhered membrane of animal biological tissue is impregnated with said dispersion to form the composite hemocompatible material.

3. The method as claimed in claim 2, wherein the glycol is a polyethylene glycol.

4. The method as claimed in claim 2, wherein the solvent is removed from the composite hemocompatible by hot extraction, extraction under vacuum, extraction in physiological saline, or a combination thereof.

5. The method as claimed in claim 2, wherein the freeze-drying rate is carried out at a rate of between 2° C./hour and 8° C./hour.

6. The composite hemocompatible material of claim 1, wherein the membrane of animal biological tissue is a freeze-dried membrane of animal biological tissue.

7. The composite hemocompatible material of claim 1, wherein the solvent is dimethylacetimide.

8. The method of claim 2, wherein the solvent is dimethylacetimide.

9. The method of claim 2, wherein the membrane of animal biological tissue treated with glycol is a chemically fixed membrane of animal biological tissue.

10. The method of claim 9, wherein the chemically fixed membrane of animal biological tissue is produced by fixing the membrane of animal biological tissue with glutaraldehyde.

11. The method of claim 2, wherein the membrane of animal biological tissue is animal pericardium.

12. The hemocompatible material as claimed in claim 1, wherein the membrane of animal biological tissue is animal pericardium.

\* \* \* \* \*